United States Patent
Lou et al.

(10) Patent No.: US 10,709,396 B2
(45) Date of Patent: Jul. 14, 2020

(54) FILTER SET OF COMPUTED TOMOGRAPHY SCANNING DEVICE AND CONTROL METHOD THEREOF

(71) Applicant: BEIJING NEUSOFT MEDICAL EQUIPMENT CO., LTD., Beijing (CN)

(72) Inventors: Shanshan Lou, Shenyang (CN); Hongbo Wang, Shenyang (CN)

(73) Assignee: Beijing Neusoft Medical Equipment Co., Ltd., Shanghai (CN)

( * ) Notice: Subject to any disclaimer, the term of this patent is extended or adjusted under 35 U.S.C. 154(b) by 123 days.

(21) Appl. No.: 15/373,811

(22) Filed: Dec. 9, 2016

(65) Prior Publication Data

US 2017/0188984 A1 Jul. 6, 2017

(30) Foreign Application Priority Data

Dec. 30, 2015 (CN) .......................... 2015 1 1020860

(51) Int. Cl.
*A61B 6/00* (2006.01)
*A61B 6/03* (2006.01)

(52) U.S. Cl.
CPC ............ *A61B 6/4035* (2013.01); *A61B 6/032* (2013.01); *A61B 6/544* (2013.01)

(58) Field of Classification Search
CPC ......... A61B 6/06; A61B 6/4035; A61B 6/544; G21K 1/10
See application file for complete search history.

(56) References Cited

U.S. PATENT DOCUMENTS

| | | | | |
|---|---|---|---|---|
| 3,917,954 A | * | 11/1975 | Boge ...................... | A61B 6/032 378/159 |
| 4,200,931 A | * | 4/1980 | Duinker ................. | A61B 6/032 378/21 |
| 4,399,550 A | * | 8/1983 | Hauck ..................... | A61B 6/06 378/157 |
| 4,686,695 A | * | 8/1987 | Macovski .............. | A61B 6/032 348/E5.089 |
| 5,107,529 A | * | 4/1992 | Boone .................. | A61B 6/4035 359/890 |

(Continued)

FOREIGN PATENT DOCUMENTS

| | | |
|---|---|---|
| JP | 2006271437 A | 10/2006 |
| JP | 2007037994 A | 2/2007 |

*Primary Examiner* — David J Makiya
*Assistant Examiner* — Soorena Kefayati
(74) *Attorney, Agent, or Firm* — Fish & Richardson P.C.

(57) ABSTRACT

A filter set of a CT scanning device and control method thereof are provided. An example of the CT scanning device includes a gantry, an X-ray generator, a filter set, a detector, and a drive motor. The filter set includes a disc, a filter disposed on the disc and having a substantially annular groove structure, and a drive shaft connected to the disc. A body thickness of the annular groove structure varies in a circumferential direction and a radial direction. A shaft axis of the drive shaft is parallel to a radiation direction of X-ray. As the drive shaft is driven by the drive motor, the disc rotates around the shaft axis, such that a region of the filter is aligned with the radiation direction of the X-ray, and a body thickness of the region corresponds to a respective X-ray attenuation for an examination region of a subject.

10 Claims, 14 Drawing Sheets

(56) References Cited

U.S. PATENT DOCUMENTS

| | | | | |
|---|---|---|---|---|
| 5,204,888 A * | 4/1993 | Tamegai | A61B 6/4035 | 378/156 |
| 6,307,918 B1 * | 10/2001 | Toth | A61B 6/032 | 378/156 |
| 6,597,758 B1 * | 7/2003 | Rosner | G01N 23/04 | 378/156 |
| 6,650,730 B2 * | 11/2003 | Bogatu | A61B 6/4042 | 378/156 |
| 7,649,981 B2 * | 1/2010 | Seppi | A61B 6/032 | 378/124 |
| 8,077,830 B2 * | 12/2011 | Brown | A61N 5/1048 | 378/156 |
| 8,686,372 B2 * | 4/2014 | Missalla | G01J 1/4257 | 250/393 |
| 8,761,347 B2 * | 6/2014 | Brown | A61N 5/1048 | 378/156 |
| 2002/0037067 A1 * | 3/2002 | Horiuchi | A61B 6/032 | 378/4 |
| 2002/0186817 A1 * | 12/2002 | Schukalski | G21K 1/04 | 378/156 |
| 2004/0264626 A1 * | 12/2004 | Besson | A61B 6/032 | 378/4 |
| 2004/0264628 A1 * | 12/2004 | Besson | A61B 6/032 | 378/5 |
| 2007/0116181 A1 * | 5/2007 | Arenson | G21K 1/043 | 378/156 |
| 2008/0279337 A1 * | 11/2008 | Yuan | A61B 6/00 | 378/156 |
| 2008/0285720 A1 * | 11/2008 | Bill | A61B 6/06 | 378/162 |
| 2010/0008558 A1 * | 1/2010 | Baeumer | A61B 6/032 | 382/131 |
| 2010/0189216 A1 * | 7/2010 | Yuan | A61B 6/06 | 378/62 |
| 2010/0246775 A1 * | 9/2010 | Yuan | G21K 1/10 | 378/158 |
| 2011/0075810 A1 * | 3/2011 | Sendai | A61B 6/4042 | 378/95 |
| 2013/0121458 A1 * | 5/2013 | Cho | A61B 6/035 | 378/5 |
| 2013/0221243 A1 * | 8/2013 | Perkins | G21K 1/04 | 250/492.3 |
| 2013/0259191 A1 * | 10/2013 | Koehler | A61B 6/032 | 378/19 |
| 2013/0343519 A1 * | 12/2013 | Ma | A61B 6/4035 | 378/54 |
| 2014/0185758 A1 * | 7/2014 | Kang | G01N 23/04 | 378/62 |
| 2015/0036792 A1 * | 2/2015 | Yi | A61B 6/032 | 378/4 |
| 2015/0078516 A1 * | 3/2015 | Ohashi | A61B 6/4042 | 378/42 |
| 2015/0201898 A1 * | 7/2015 | Machida | A61B 6/0421 | 378/20 |
| 2015/0312998 A1 * | 10/2015 | Tamura | A61B 6/482 | 378/5 |
| 2016/0113617 A1 * | 4/2016 | Herrmann | A61B 6/42 | 378/207 |
| 2016/0211045 A1 * | 7/2016 | Jeon | G21K 1/10 | |
| 2017/0119337 A1 * | 5/2017 | Nekovar | A61B 6/5288 | |

\* cited by examiner

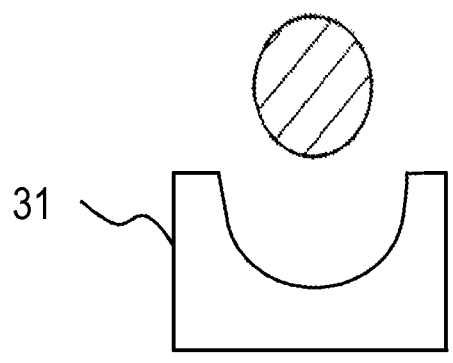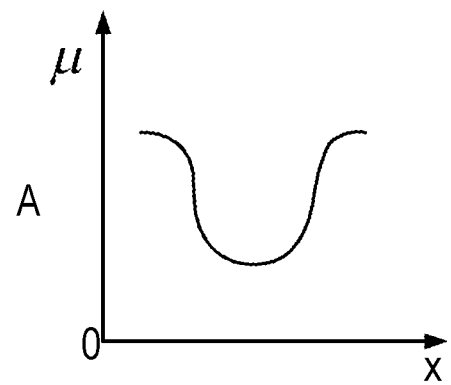
FIG. 7A  FIG. 7B
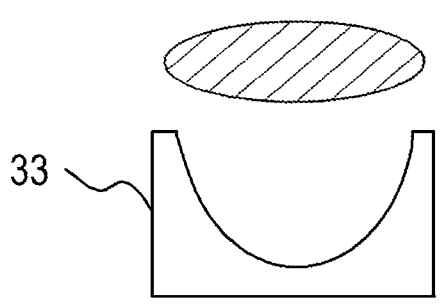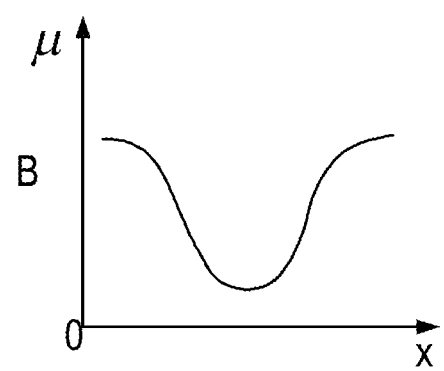
FIG. 7C  FIG. 7D
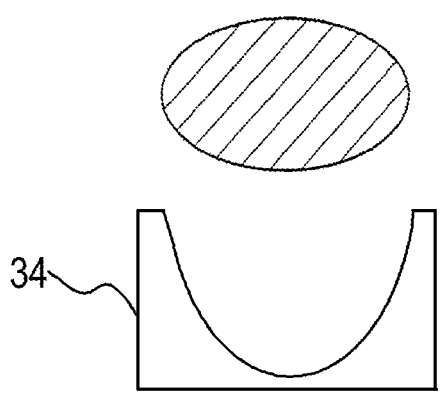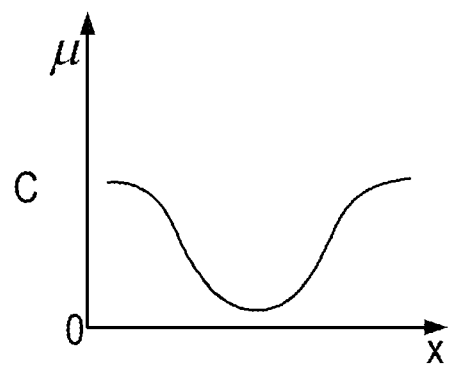
FIG. 7E  FIG. 7F

FILTER SET OF COMPUTED TOMOGRAPHY SCANNING DEVICE AND CONTROL METHOD THEREOF

CROSS REFERENCE TO RELATED APPLICATIONS

This application claims priority under 35 U.S.C. § 119 to Chinese Patent Application No. 201511020860.2, filed on Dec. 30, 2015. The content of this priority application is hereby incorporated by reference in its entirety.

TECHNICAL FIELD

The present disclosure relates to a filter set of computed tomography (CT) scanning device and control method thereof.

BACKGROUND

In a computed tomography (CT) scanning process, it may dispose a filter between an X-ray source and a patient's examination region to filter out low-energy rays that have no positive effect for reconstructing a CT image, and to make energy distribution of the projection rays to the patient more uniform, thereby to obtain CT images with better quality and to reduce the patient's radiation dose.

SUMMARY

One aspect of the present disclosure features a filter set of a computed tomography (CT) scanning device, comprising: a disc; a filter disposed on the disc, the filter having a substantially annular groove structure, a body thickness of the annular groove structure varying in a circumferential direction and a radial direction; and a drive shaft connected to the disc, a shaft axis of the drive shaft being parallel to a radiation direction of X-ray of the CT scanning device, the disc being configured to rotate around the shaft axis of the drive shaft.

In some implementations, the filter comprises a plurality of grooves separable in the circumferential direction of the annular groove structure. In some implementations, the filter comprises an annular groove, and a body thickness of the annular groove continuously varies in the circumferential direction. In some implementations, the filter comprises a plurality of annular grooves separable in the radial direction, and a body thickness of each annular groove continuously varies in the circumferential direction. In some implementations, a radial cross-sectional shape of the annular groove structure of the filter is a bow tie.

Another aspect of the present disclosure features a computed tomography (CT) scanning device comprising: a gantry; an X-ray generator disposed in an interior of the gantry and configured to rotate together with the gantry around a body axis of a subject; a filter set disposed in the interior of the gantry, the filter set being configured to be located between the X-ray generator and the subject and to rotate together with the gantry around the body axis of the subject, the filter set comprising: a disc; a filter disposed on the disc, the filter having a substantially annular groove structure, a body thickness of the annular groove structure varying in a circumferential direction and a radial direction; and a drive shaft connected to the disc, a shaft axis of the drive shaft being parallel to a radiation direction of X-ray generated by the X-ray generator, the disc being configured to rotate around the shaft axis; a detector disposed in the interior of the gantry and located at an opposite side of the X-ray generator, the detector being configured to rotate together with the gantry around the body axis of the subject and to receive the X-ray generated by the X-ray generator and filtered by the filter set; and a drive motor connected to the drive shaft and configured to drive the drive shaft such that the disc rotates around the shaft axis of the drive shaft.

In some implementations, the filter comprises a plurality of grooves separable in the circumferential direction of the annular groove structure. In some implementations, the filter comprises an annular groove, and a body thickness of the annular groove continuously varies in the circumferential direction. In some implementations, the filter comprises a plurality of annular grooves separable in the radial direction, and a body thickness of each annular groove continuously varies in the circumferential direction.

The gantry can be a substantially annular structure, and the filter set can be located inside the gantry and opposite to the X-ray generator in a radial direction of the substantially annular structure. The filter can be located between an anode focus and a radiation window in an interior cavity of the X-ray generator.

A third aspect of the present disclosure features a method of controlling a filter set of a computed tomography (CT) scanning device. The method comprises: obtaining information of an examination region of a subject; and controlling movement of a disc of the filter set based on the determined information of the examination region, such that a target region of a filter of the filter set disposed on the disc is aligned with a radiation direction of an X-ray of the CT scanning device, wherein a body thickness of the target region of the filter corresponds to a respective X-ray attenuation for the examination region. The filter has a substantially annular groove structure, a body thickness of the annular groove structure varying in a circumferential direction and a radial direction, and the disc is connected to a drive shaft of the filter set that has a shaft axis parallel to the radiation direction of the X-ray, the disc being configured to rotate around the shaft axis.

In some implementations, the filter comprises a plurality of grooves separable in the circumferential direction of the annular groove structure, and controlling the movement of the disc of the filter set comprises: controlling the disc to rotate around the shaft axis of the drive shaft such that a target groove of the plurality of grooves is aligned with the radiation direction of the X-ray, wherein a body thickness of the target groove corresponds to the respective X-ray attenuation for the examination region.

In some implementations, the filter comprises an annular groove, and a body thickness of the annular groove continuously varies in the circumferential direction, and controlling the movement of the disc of the filter set comprises: controlling the disc to continuously rotate around the shaft axis of the drive shaft based on respective X-ray attenuations under different projection angles for the examination region.

In some implementations, the filter comprises a plurality of annular grooves separable in the radial direction, and a body thickness of each annular groove continuously varies in the circumferential direction, and controlling the movement of the disc of the filter set comprises: controlling the disc to move along a body axis of the subject such that a target annular groove of the plurality of annular grooves is aligned with the radiation direction of the X-ray, wherein the body thickness of the target annular groove corresponds to the respective X-ray attenuation for the examination region; and controlling the disc to continuously rotate around the shaft axis of the drive shaft based on respective X-ray attenuations under different projection angles for the examination region.

A fourth aspect of the present disclosure features an apparatus for controlling a filter set of a computed tomography (CT) scanning device. The apparatus comprises: a processor; and a non-transitory computer readable storage medium storing machine executable instructions that correspond to a control logic of the filter set and upon such execution cause the processor to perform operations comprising: obtaining information of an examination region of a subject; and controlling movement of a disc of the filter set based on the information of the examination region, such that a target region of a filter of the filter set disposed on the disc is aligned with a radiation direction of an X-ray of the CT scanning device, wherein a body thickness of the target region of the filter corresponds to a respective X-ray attenuation for the examination region. The filter has a substantially annular groove structure, a body thickness of the annular groove structure varying in a circumferential direction and a radial direction, and the disc of the filter set is connected to a drive shaft of the filter set that has a shaft axis parallel to the radiation direction of the X-ray, the disc being configured to rotate around the shaft axis.

In some implementations, the filter comprises a plurality of grooves separable in the circumferential direction of the annular groove structure, and controlling the movement of the disc of the filter set comprises: controlling the disc to rotate around the shaft axis of the drive shaft such that a target groove of the plurality of grooves is aligned with the radiation direction of the X-ray, wherein a body thickness of the target groove corresponds to the respective X-ray attenuation for the examination region.

In some implementations, the filter comprises an annular groove, and a body thickness of the annular groove continuously varies in the circumferential direction, and controlling the movement of the disc of the filter set comprises: controlling the disc to continuously rotate around the shaft axis of the drive shaft based on respective X-ray attenuations under different projection angles for the examination region.

In some implementations, the filter comprises a plurality of annular grooves separable in the radial direction, and a body thickness of each annular groove continuously varies in the circumferential direction, and controlling the movement of the disc of the filter set comprises: controlling the disc to move along a body axis of the subject so that a target annular groove of the plurality of annular grooves is aligned with the radiation direction of the X-ray, wherein the body thickness of the target annular groove corresponds to the respective X-ray attenuation for the examination region; and controlling the disc to continuously rotate around the shaft axis of the drive shaft based on respective X-ray attenuations under different projection angles for the examination region.

A further aspect of the present disclosure features a non-transitory computer readable storage medium storing instructions that are executable by a processor and upon such execution cause the processor to perform actions of the method of controlling a filter set of a computed tomography (CT) scanning device mentioned above.

The details of one or more embodiments of the subject matter described in the present disclosure are set forth in the accompanying drawings and description below. Other features, aspects, and advantages of the subject matter will become apparent from the description, the drawings, and the claims.

BRIEF DESCRIPTION OF DRAWINGS

Features of the present disclosure are illustrated by way of example and not limited in the following figures, in which like numerals indicate like elements.

FIG. 7A is a radial cross-sectional view of a filter region corresponding to a patient's head according to an example of the present disclosure.

FIG. 7B is a schematic view of the corresponding X-ray attenuation curve according to an example of FIG. 7A of the present disclosure.

FIG. 7C is a radial cross-sectional view of a filter region corresponding to a patient's shoulder according to an example of the present disclosure.

FIG. 7D is a schematic view of the corresponding X-ray attenuation curve according to an example of FIG. 7C of the present disclosure.

FIG. 7E is a radial cross-sectional view of a filter region corresponding to a patient's thoracic cavity according to an example of the present disclosure.

FIG. 7F is a schematic view of the corresponding X-ray attenuation curve according to an example of FIG. 7E of the present disclosure.

DETAILED DESCRIPTION

A computed tomography (CT) scanning device may comprise a scanning device, a computer system, and an examining table. The scanning device may be used to scan a patient and obtain raw data of the patient's examination region. The examining table may be used to send the patient to a predetermined or appropriate location. In some CT systems, the examining table may be an option. The computer system may be used to control the entire CT scanning device which may be used to turn the X-ray generator and the detector on and off at right moments, to receive scanning parameters for initialization configuration, to obtain the raw data by the scanning device, to control the operations of the examining table and gantry, and to reconstruct the CT images according to the raw data. In one example, the computer system may be used to display images, e.g., to display the reconstruction CT images.

Figure 1:
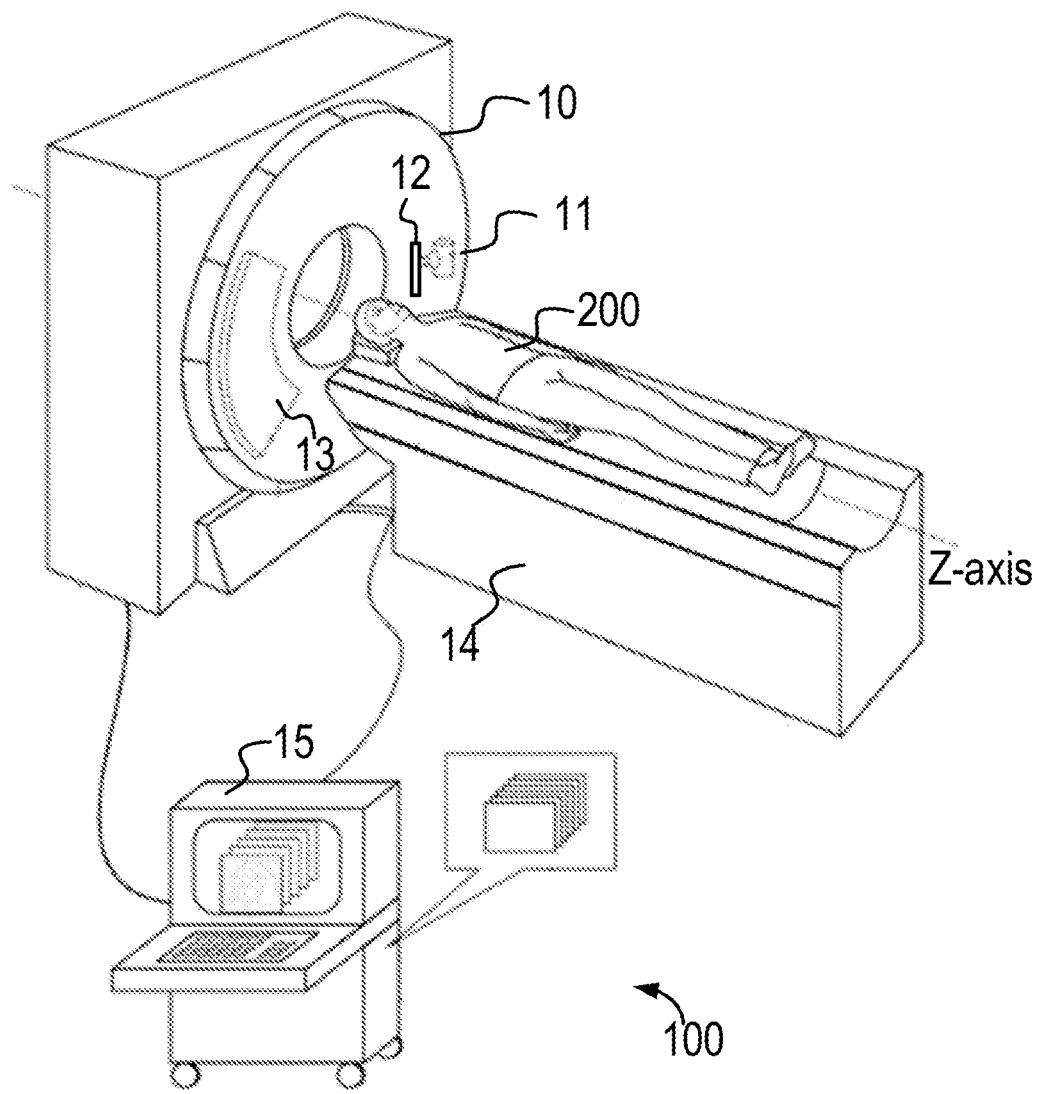
FIG. 1 is a usage schematic view of a CT scanning device according to an example of the present disclosure.
Figure 2:
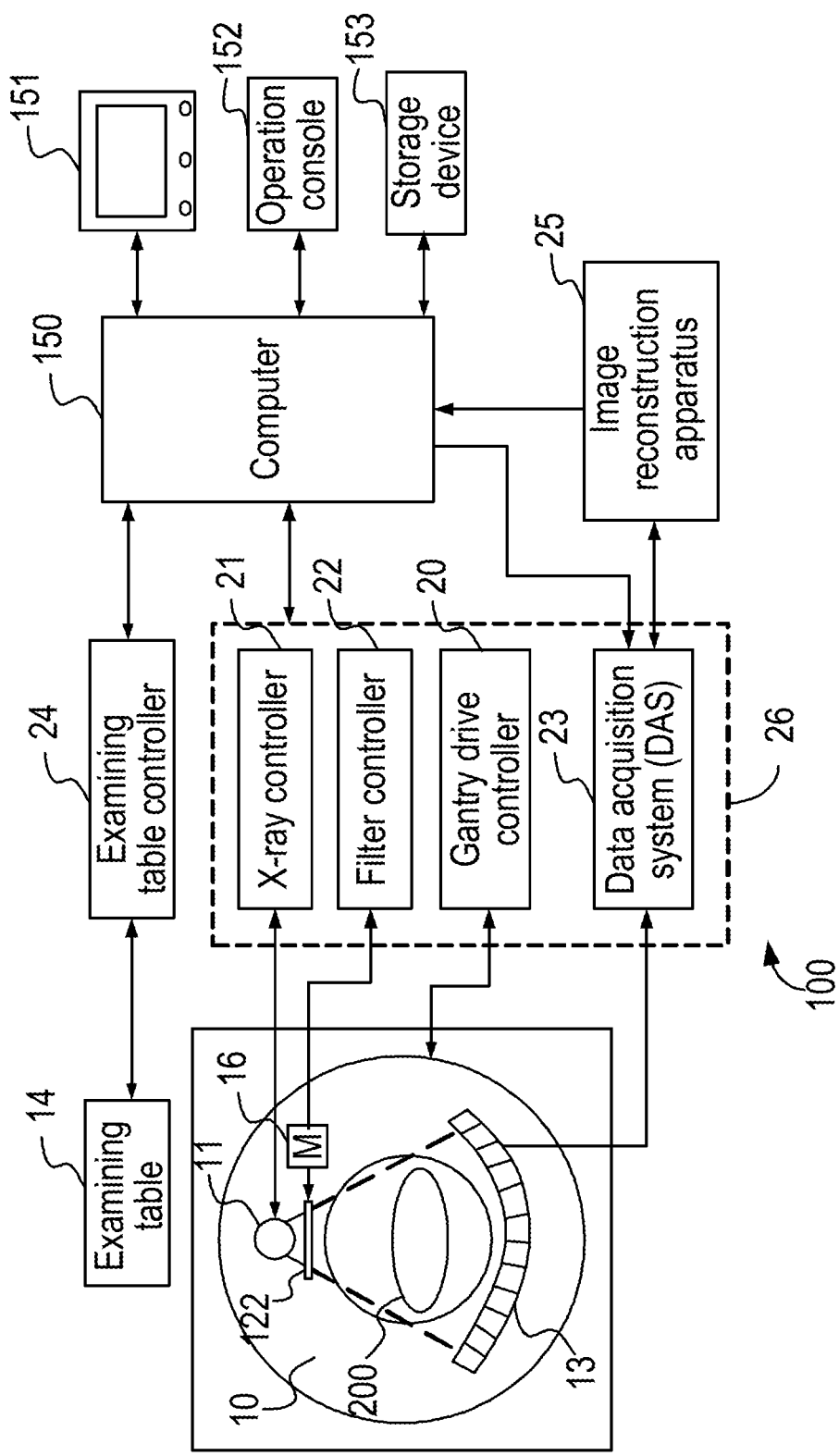
FIG. 2 is a schematic system structure view of a CT scanning device according to an example of the present disclosure.

FIG. 1 is a usage schematic view of a CT scanning device according to an example of the present disclosure. FIG. 2 is a schematic system structure view of the CT scanning device according to an example of the present disclosure. Referring to FIG. 1 and FIG. 2, the CT scanning device 100 may comprise a scanning device, an examining table 14, and a computer system 15.

The scanning device may comprise a gantry 10. The gantry 10 may be an annular structure which can be rotated around Z-axis to perform a CT scan for a specific examination region of a patient 200. Z-axis may be the direction of a body axis of the patient 200, which is the virtual line between the head and leg of the patient 200, as shown in FIG. 1. The examining table 14 may be capable of carrying the patient 200 along the Z-axis direction through the gantry 10.

Figure 3:
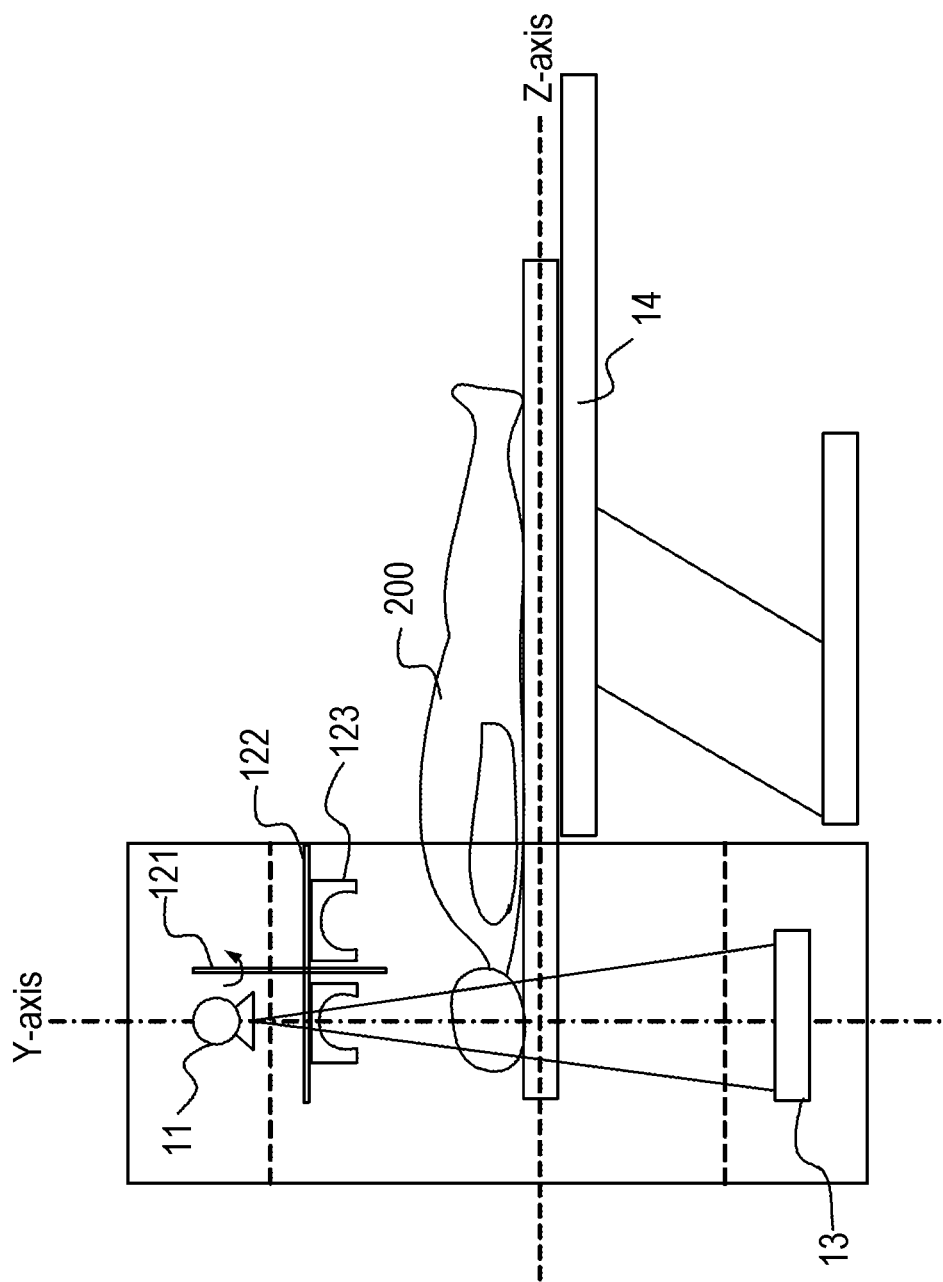
FIG. 3 is a schematic view of a CT scanning device according to an example of the present disclosure.

As shown in FIG. 2, the gantry 10 may be mounted with an X-ray generator 11. The X-ray generator 11 may emit X-rays in a direction which is vertical to the Z-axis, e.g., the radiation direction of X-rays may be in the direction of the Y-axis (as FIG. 3 shows). Where, the Y-axis may indicate an upwards direction vertical to the Z-axis with taking the rotating center of the gantry 10 as an origin. In the gantry 10, a detector 13 for receiving the X-ray may be disposed in a location opposite to the X-ray generator 11. As shown in FIG. 1, a filter set 12 may be disposed in the interior of the gantry 10. For example, the filter set 12 may be disposed on a disc 122, and the disc 122 may be located inside of the gantry 10 and be opposite to the X-ray generator 11 in the radial direction. In a CT scanning process, the filter set 12 may be rotated together with the X-ray generator 11 around the Z-axis. The X-ray generated by the X-ray generator 11 may be attenuated by the filter set 12, and then may act upon the examination region of the patient 200. The filter set 12 may be driven by a filter drive motor 16 to move, e.g., translate or rotate, in relative to the X-ray generated by the X-ray generator 11, such that a specific filter and/or a specific filter region of the filter set 12 may be moved to be aligned with a radiation direction of the X-ray.

In a CT scanning process, the cross-sections for different examination regions are different from each other and the thicknesses being penetrated by the X-ray of the same examination region under different scanning angles may be also different from each other, such that the filter of the filter set 12 may be required to meet the requirement of the X-ray attenuation for different examination regions and/or the requirement of the X-ray attenuation for the same examination region under different projection angles. Where, each of the projection angles is a respective angle between the radiation direction of the X-ray and a horizontal axis of the examination region which is parallel to the X-axis as show in FIG. 4.

As shown in FIG. 2, the computer system 15 may comprise a computer 150, an examining table controller 24, an image reconstruction apparatus 25, and a control apparatus 26. The control apparatus 26 may be used to control the gantry 10 for driving the X-ray generator 11 and the detector 13 to rotate around the Z-axis, to control the X-ray generator 11 for radiating the X-rays during rotation, and to control the movement of the filter set 12.

In one example, the control apparatus 26 may comprise an X-ray controller 21, a filter controller 22, a gantry drive controller 20, and a data acquisition system (DAS) 23. The X-ray controller 21 may be used to provide energy and timing signals for the X-ray generator 11. The filter controller 22 may be used to control the start position and rotation speed of the filter set 12. The gantry drive controller 20 may be used to control rotation speed and the start position of the gantry 10. The DAS 23 may be used to obtain the data acquired by the detector 13, to convert the data acquired to the digital signal, and output the digital signal to the image reconstruction apparatus 25.

The image reconstruction apparatus 25 may be used to reconstruct the images according to the digital signal outputted by the DAS 23 to obtain the CT images.

The computer 150 may be used to convert the commands and parameters inputted by the operator to the control signals, or to transmit messages to the control apparatus 26 and/or the examining table controller 24. The computer 150 may receive and store the reconstruction CT images reconstructed by the image reconstruction apparatus 25.

According to one example, the computer system 15 may further comprise a display 151, an operation console 153, and a storage device 153. The display 151 may be used to display the reconstruction CT images and the corresponding data. The operation console 152 may be used to receive the commands and scan parameters inputted by the operator. The storage device 153 may be used to store a large amount of the reconstruction CT images.

According to the aforementioned CT scanning device, the present disclosure provides a filter set. In conjunction with FIG. 3 to FIG. 10, the following descriptions may provide detail disclosures for the filter set.

Figure 4:
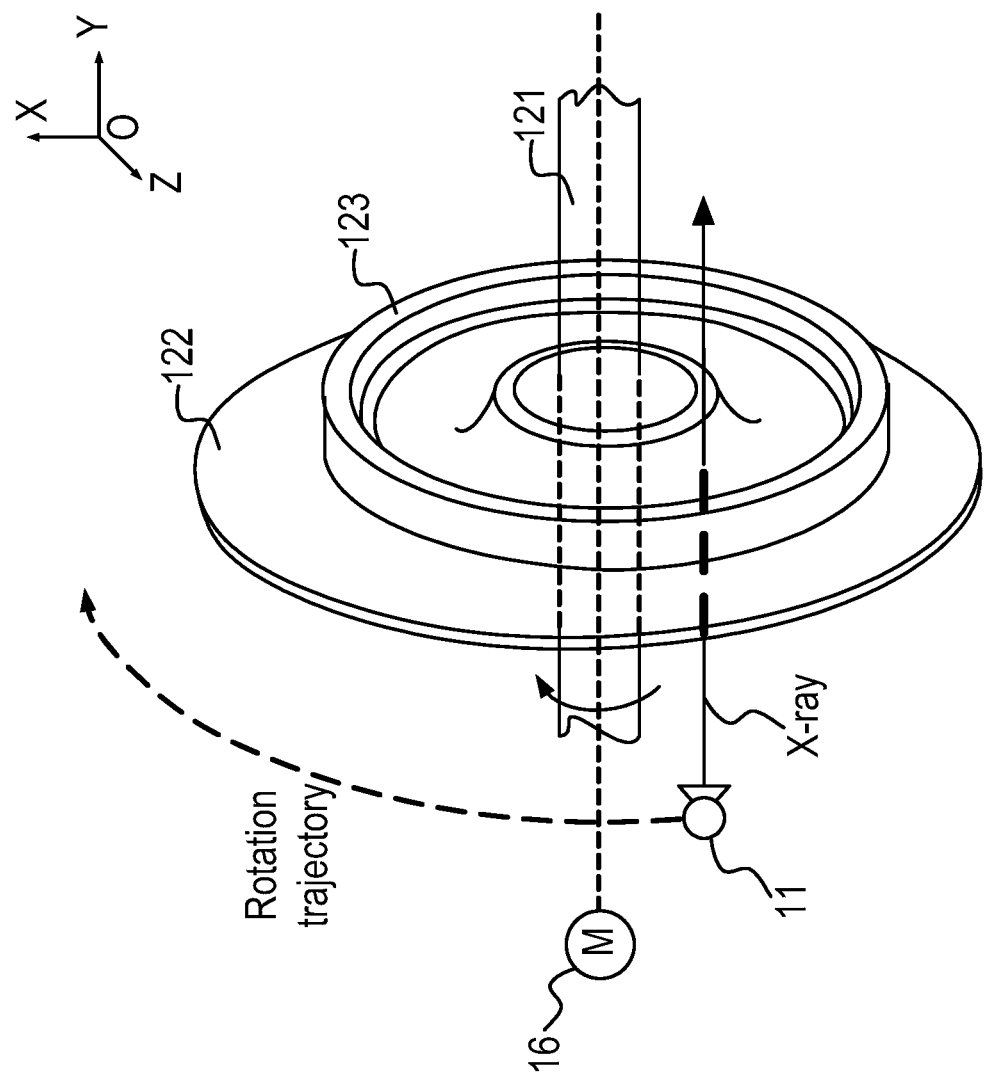
FIG. 4 is a schematic view of a filter set according to an example of the present disclosure.
Figure 5:
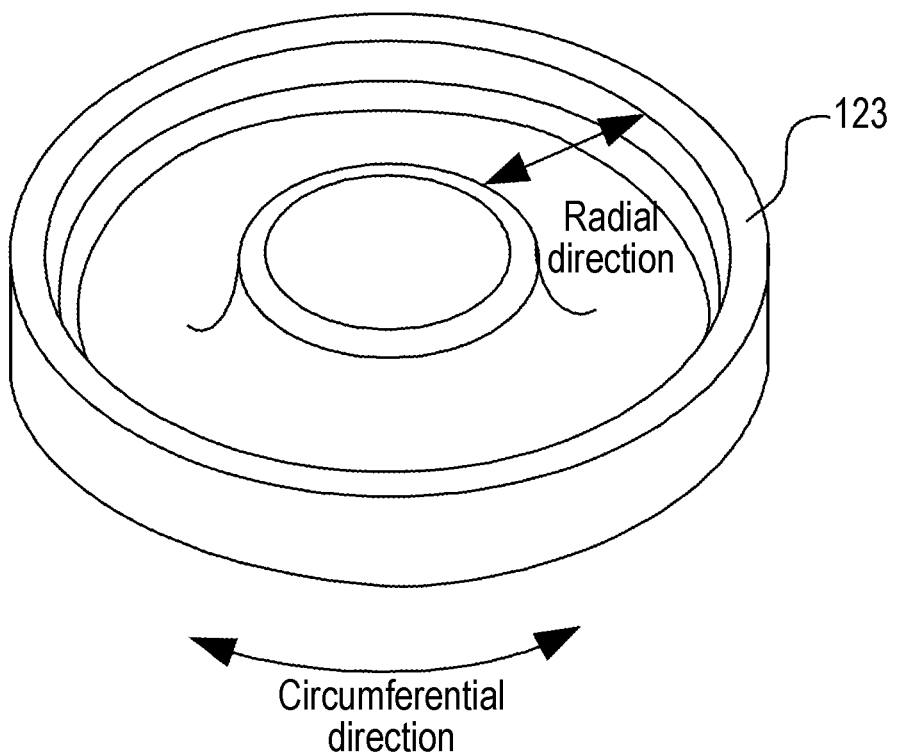
FIG. 5 is a schematic diagram of a filter according to an example of the present disclosure.

FIG. 3 is a schematic view of a CT scanning device according to an example of the present disclosure. FIG. 4 is a schematic view of a filter set according to an example of the present disclosure. FIG. 5 is a schematic diagram of a filter according to an example of the present disclosure. Referring to the structure of the filter set 12 shown in FIG. 3 to FIG. 5, the filter set 12 may comprise a filter 123, a disc 122, and a drive shaft 121. In some implementations, the filter 123 is an annular structure disposed on the disc 122. A body thickness of the annular structure varies in a circumferential direction and a radial direction. The body thickness at a specific position of the annular structure is based on the specific position in both the circumferential direction and the radial direction of the annular structure. In some examples, the annular structure is an annular groove, and the body thickness of the annular groove varies in the circumferential direction and the radial direction of the annular groove, such that the body thickness of the annular groove may meet the requirement of X-ray attenuation for an examination region. In some cases, the bottom of the annular groove may be aligned with a radiation direction of the X-ray center beam, such that the X-ray center beam may penetrate through the bottom of the annular groove. Hereinafter, the radiation direction of the X-ray center beam may be referred to the radiation direction of the X-ray. The disc 122 is connected to the drive shaft 121. The filter drive motor 16 may drive the drive shaft 121 so as to drive the disc 122 to rotate around a shaft axis of the drive shaft 121. The shaft axis of the drive shaft 121 is parallel to the radiation direction of X-ray, wherein the radiation direction of X-ray is in parallel to the Y-axis direction shown in FIG. 4.

In one example of the present disclosure, one end of the drive shaft 121 may be fixedly connected to the central location of disc 122. In another example, one end of the drive shaft 121 may be through the central location of the disc 122, and the drive shaft 121 may be fixedly connected to the disc 122 at the central location of the disc 122. As shown in FIG. 4, another end of the drive shaft 121 may be connected to the filter drive motor 16. The drive shaft 121 is driven by the filter drive motor 16, and then the drive shaft 121 may drive the disc 122 to rotate around the shaft axis of the drive shaft 121.

In another example of the present disclosure, one end of the drive shaft 121 may be flexibly connected to the central location of disc 122. Another end of the drive shaft 121 may be connected to the filter drive motor 16. The drive shaft 121 is driven by the filter drive motor 16, and then the drive shaft 121 may drive the disc 122 to rotate around the shaft axis of the drive shaft 121.

The filter set 12 may be regarded as a whole piece to be disposed inside the interior of the gantry 10. The filter set 12 may be rotated together with the gantry 10 around the Z-axis. In one example of the present disclosure, the filter set 12 can be driven by the filter drive motor 16 to have a movement corresponding to the X-ray generator 11. For example, the movement may be translation or rotation. A specific filter or a specific filter region of the filter set 12 may be moved to be aligned with a radiation direction of the X-ray.

FIG. 5 shows an annular groove structure of a filter, where a body thickness of the annular groove structure of the filter varies in a circumferential direction and a radial direction. In one example of the present disclosure, according to the variation of the body thickness, the filter with the annular groove structure may be divided into a separable-shape filter and a continuous-shape filter.

Figure 6:
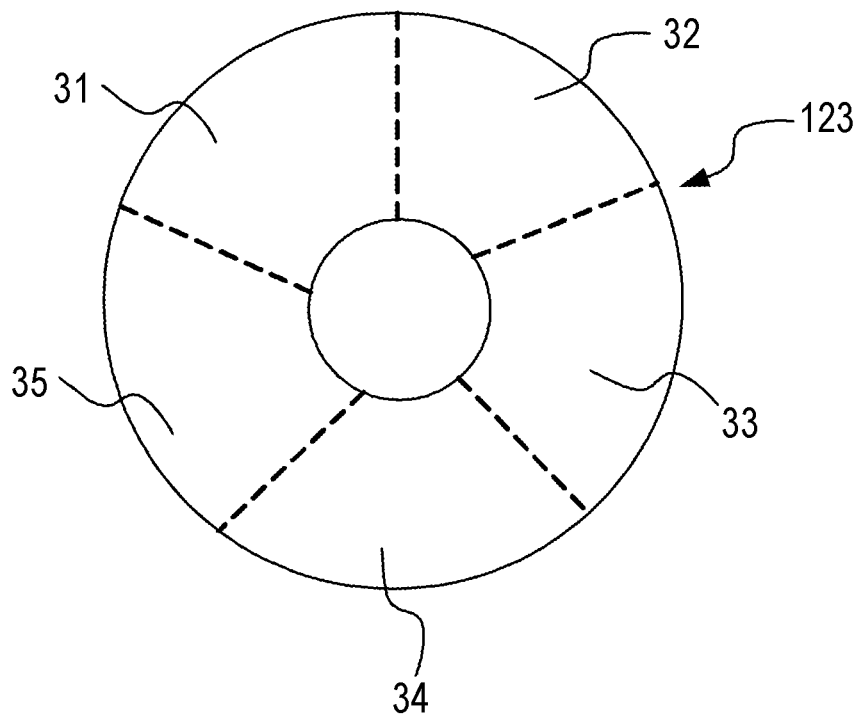
FIG. 6 is a schematic view of a separable-shape filter according to an example of the present disclosure.

FIG. 6 is a schematic view of a separable-shape filter according to an example of the present disclosure. As shown in FIG. 6, according to the distribution of the body thickness, the separable-shape filter may be divided into a plurality of filter regions. The body thickness of each filter region may depend on the requirement of X-ray attenuation for the examination region. For example, the filter 123 may comprise a plurality of independent grooves which are separated from each other in the circumferential direction. The respective body thicknesses of these grooves may meet the requirements of X-ray attenuation for different examination regions. As shown in FIG. 6, the filter 123 may comprise a head filter region 31, a neck filter region 32, a shoulder filter region 33, a thoracic cavity filter region 34, a trunk filter region 35, and so on. According to the requirements, the separable-shape filter of the present disclosure may further comprise more filter regions for different examination regions, for example, a lumbar spine filter region, a pelvis filter region, an extremities filter region, etc.

FIGS. 7A to 7F schematically show three cross-sectional views in a radial direction of three filter regions corresponding to three examination regions and corresponding X-ray attenuation curves.

FIG. 7A is a radial cross-sectional view of a filter region corresponding to a patient's head according to an example of the present disclosure. FIG. 7B is a schematic view of the corresponding X-ray attenuation curve according to an example of FIG. 7A of the present disclosure. When the scanning device is used to perform a CT scanning for the patient's head, the filter drive motor 16 may drive the disc 122 to rotate around the shaft axis of the drive shaft 121 until the head filter region 31 of the separable-shape filter 123 shown in FIG. 6 being aligned with the radiation direction of the X-ray. Therefore, the X-ray center beam may penetrate through the center position of the head filter region 31. Curve A shown in FIG. 7B is an X-ray attenuation curve corresponding to the head filter region 31. As shown in FIG. 7B, the amount of X-ray attenuation μ is varied in the radial direction, e.g., X-axis direction, according to the body thickness of the head filter region 31.

FIG. 7C is a radial cross-sectional view of a filter region corresponding to a patient's shoulder according to an example of the present disclosure. FIG. 7D is a schematic view of the corresponding X-ray attenuation curve according to an example of FIG. 7C of the present disclosure. As performing a CT scanning for the patient's shoulder by using the scanning device, the filter drive motor 16 may drive the disc 122 to rotate around the shaft axis of the drive shaft 121 until the shoulder filter region 33 of the separable-shape filter 123 shown in FIG. 6 being aligned with the radiation direction of the X-ray. Therefore, the X-ray center beam may penetrate through the center position of the shoulder filter region 33. Curve B shown in FIG. 7D is an X-ray attenuation curve corresponding to the shoulder filter region 33. As shown in FIG. 7D, the amount of X-ray attenuation μ is varied in the radial direction, e.g., X-axis direction, according to the body thickness of the shoulder filter region 33.

FIG. 7E is a radial cross-sectional view of a filter region corresponding to a patient's thoracic cavity according to an example of the present disclosure. FIG. 7F is a schematic view of the corresponding X-ray attenuation curve according to an example of FIG. 7E of the present disclosure. As performing a CT scanning for the patient's thoracic cavity by using the scanning device, the filter drive motor 16 may drive the disc 122 to rotate around the shaft axis of the drive shaft 121 until the thoracic cavity filter region 34 of the separable-shape filter 123 shown in FIG. 6 being aligned with the radiation direction of the X-ray. Therefore, the X-ray center beam may penetrate through the center position of the shoulder filter region 33. Curve C shown in FIG. 7F is an X-ray attenuation curve corresponding to the thoracic cavity filter region 34. As shown in FIG. 7F, the amount of X-ray attenuation μ is varied in the radial direction, e.g., X-axis direction, according to the body thickness of the thoracic cavity filter region 34.

From FIG. 7A to FIG. 7F, owing to the shapes of cross-sectional view for different examination regions being different from each other, the X-ray attenuation curves of the filter regions of the filter 123 may be also different as the X-ray penetrates through the filter regions corresponding to different examination regions. Thus, the requirements of X-ray attenuation for different examination regions can be met.

In one example, under the control of the filter controller 22, the filter drive motor 16 may drive the disc 122 to rotate around the shaft axis of the drive shaft 121, until the filter region of the separable-shape filter 123 corresponding to the examination region being aligned with the radiation direction of the X-ray. After beginning the scan, the disc 122 may no longer rotate around the shaft axis of the drive shaft 121, that is, the position of the filter may be maintained substantially the same. Thus, during the scanning, the filter region corresponding to the examination region may be rotated together with the X-ray generator 11 and the detector 13 around the Z-axis. Therefore, the X-ray may penetrate through the body of the filter region corresponding to the examination region and may reach the examination region.

The separable-shape filter 123 of the present disclosure can provide different filter regions for different examination regions, which enables to increase the CT scan efficiency and to make the operation relatively simple.

In another example of the present disclosure, the present disclosure may provide a continuous-shape filter. The body thickness of the continuous-shape filter varies in the circumferential direction and the radial direction. The variation of the body thickness may meet the requirement of X-ray attenuation for the same examination region under different projection angles. For example, the continuous-shape filter may comprise an annular groove. The body thickness of the annular groove may be continuously varied in the circumferential direction so as to meet the requirement of X-ray attenuation for a specific examination region under different projection angles. Wherein, the projection angle may be the angle between the radiation direction of the X-ray and the horizontal axis of the examination region, that is, the angle between the radiation direction of the X-ray and X-axis.

Figure 8A:
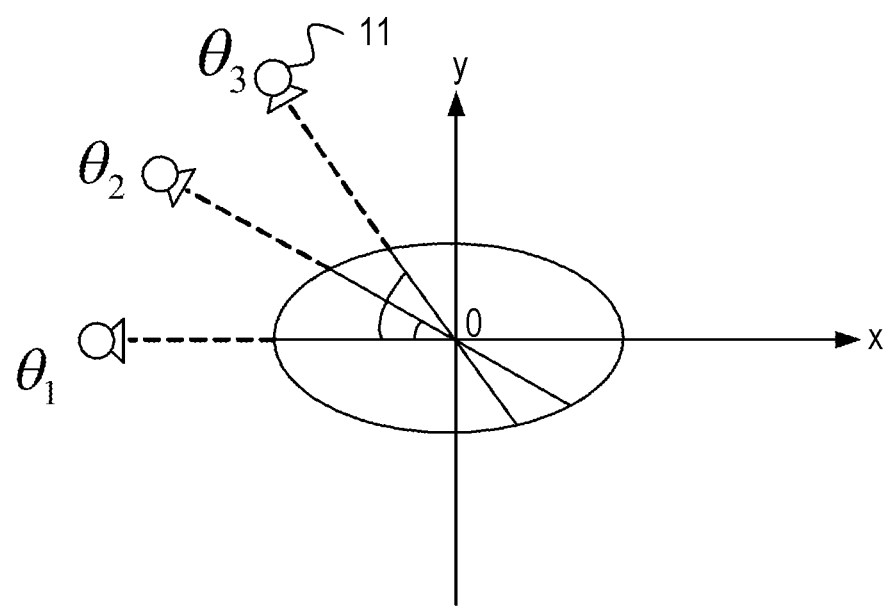
FIG. 8A to FIG. 8G schematically show different cross-sectional views in radial direction of the same examination region under different projection angles and the corresponding X-ray attenuation curves.

Referring to FIG. 8A, in case of the examination region being the chest of a patient for example, in the rotation trajectory of one rotation circle of the X-ray generator 11, owing to the shape of the cross-sectional view of the chest being similar to an ellipse, the thicknesses of human body tissue which may be penetrated through by the X-ray are not the same under different projection angles. Accordingly, the requirements of X-ray attenuation of the filters may be different under different projection angles. The adjustment of the X-ray attenuation may be accomplished according to the body thickness of the filter. For example, in the projection angle which may be required more X-ray attenuation, the corresponding body thickness of the filter may be thicker. In contrast, in the projection angle which may be required less X-ray attenuation, the corresponding body thickness of the filter may be thinner.

Figure 8B:
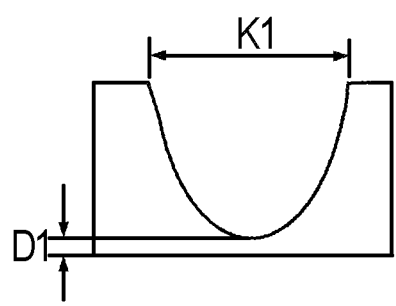
Figure 8C:
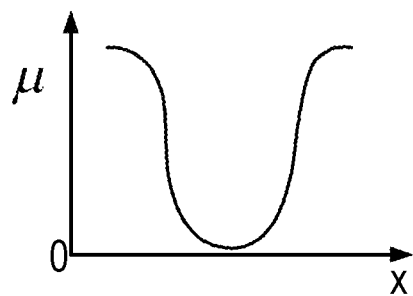

FIGS. 8B to 8G schematically show three cross-sectional views in radial direction under three different projection angles and the corresponding X-ray attenuation curves. The projection angle θ may be the angle between the X-ray center beam radiated by the X-ray generator 11 and X-axis of the examination region. It may assume that $\theta_1=0°$, $\theta_2=30°$, and $\theta_3=60°$. As shown in FIG. 8A, when the X-ray center beam coincides with the ellipse long axis of the chest, i.e., the projection angle being $\theta_1$ (=0°), the distance that X-ray penetrates through the human body is maximum. FIG. 8B is a radial cross-sectional view of a filter corresponding to the projection angle $\theta_1$ according to an example of the present disclosure. As shown in FIG. 8B, the thickness of intermediate bottom of the filter is minimum so that the attenuation of X-ray by the filter may be the minimum under the projection angle. In addition, the thickness of the patient's chest in Y-axis direction is the minimum under the projection angle. The opening width K1 of the groove may be the minimum, wherein the groove is shown in the radial cross-sectional view in FIG. 8B. FIG. 8C is a schematic view of an X-ray attenuation curve corresponding to the radial cross-sectional view under the projection angle being $\theta_1$.

Figure 8D:
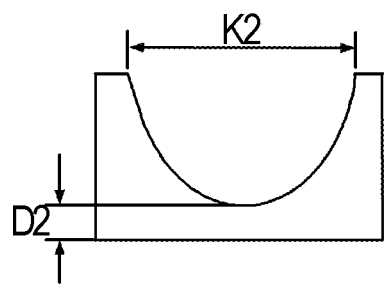
Figure 8E:
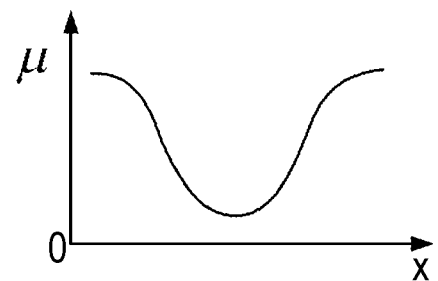

With increasing of the projection angle, as the projection angle being $\theta_2$ (=30°), the distance that X-ray penetrates through the human body may become smaller. FIG. 8D is a radial cross-sectional view of the filter corresponding to the projection angle $\theta_2$ according to an example of the present disclosure. In comparison with FIG. 8B, the thickness of intermediate bottom of the filter shown in FIG. 8D is larger than the thickness of intermediate bottom of the filter shown in FIG. 8B. Thus, the attenuation of X-ray by the filter in FIG. 8D may be larger than the attenuation in FIG. 8B. In comparison with the projection angle $\theta_1$, the thickness of the patient's chest projected in Y-axis direction may be become larger under the projection angle $\theta_2$. The opening width K2 of the groove may be larger than the opening width K1 of the groove. FIG. 8E is a schematic view of an X-ray attenuation curve corresponding to the radial cross-sectional view under the projection angle being $\theta_2$.

Figure 8F:
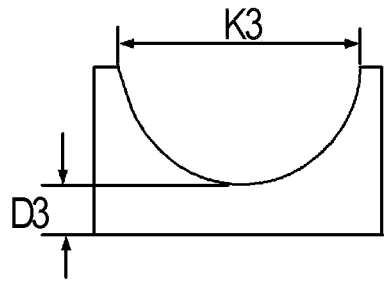
Figure 8G:
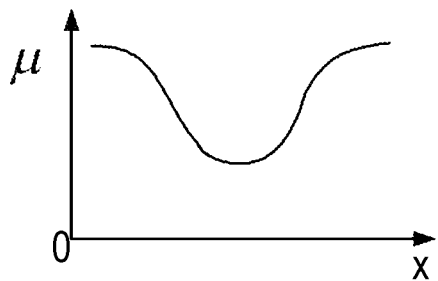

With more increasing of the projection angle, as the projection angle being $\theta_3$ (=60°), the distance that X-ray penetrates through the human body may continuously become smaller. FIG. 8F is a radial cross-sectional view of a filter corresponding to the projection angle $\theta_3$ according to an example of the present disclosure. In comparison with FIG. 8D, the thickness of intermediate bottom of the filter shown in FIG. 8F is larger than the thickness of intermediate bottom of the filter shown in FIG. 8D. Thus, the attenuation of X-ray by the filter in FIG. 8F may be larger than the attenuation in FIG. 8D. In comparison with the projection angle $\theta_2$, the thickness of the patient's chest projected in Y-axis direction may be become larger under the projection angle $\theta_3$. The opening width K3 of the groove may be larger than the opening width K2 of the groove. FIG. 8G is a schematic view of an X-ray attenuation curve corresponding to the radial cross-section of a filer under the projection angle being $\theta_3$.

With the variations of the projection angles, as the X-ray penetrates through the radial cross-section of a filter, owing to the X-ray attenuation curves corresponding to the radial cross-section under different projection angles being different, the requirements of the X-ray attenuation for the same examination region under different projection angles may be met. Accordingly, the shapes of the radial cross-sections of a filter corresponding to the other projection angles may be determined, and the shapes of the radial cross-sections of the filter corresponding to the other examination regions under different projection angles can be also determined.

In one example, the gantry drive controller 20 may drive the X-ray generator 11, the filter set 12, and the detector 13 to rotate around the Z-axis. As performing the CT scanning for an examination region of the patient 200, e.g., the CT scanning for the chest, under the control of the filter controller 22, the filter drive motor 16 may drive the disc 122 to rotate around the shaft axis of the drive shaft 121. In the CT scanning process, the X-ray keeps penetrating through the body of the filter 123 no matter how the disc 122 is rotated. The radial cross-section of the filter 123 penetrated by the X-ray may vary according to a change of the projection angle.

The continuous-shape filter of the present disclosure can meet the requirement of the X-ray attenuation for the same examination region under different projection angles, which enables to optimize the intensity distribution of the X-ray to increase the quality of CT images.

In another example, under the condition of the area of the disc 122 being sufficient large, the disc 122 may be arranged with two or more continuous-shape filters which are respectively corresponding to different examination regions. The aforementioned architecture may be called the multi-channel continuous-shape filter. For example, the filter 123 may comprise a plurality of separable annular grooves in the radial direction, wherein the body thickness of the annular grooves may vary in the circumferential direction. The annular grooves are independent and separated from each other in the radial direction.

Figure 9:
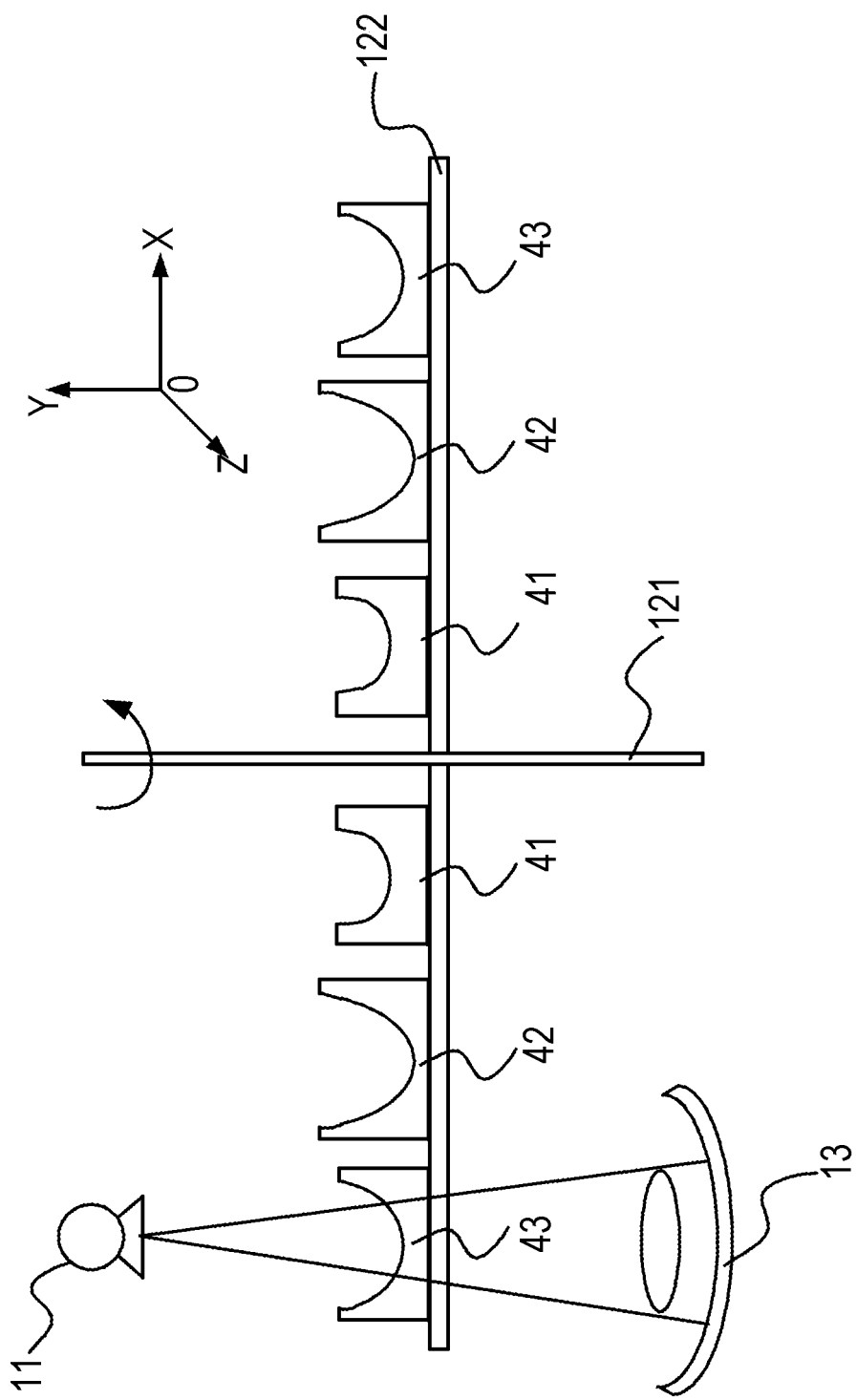
FIG. 9 schematically shows a cross-sectional view taken along the XY plane of a multi-channel continuous-shape filter according to an example of the present disclosure.

FIG. 9 schematically shows a cross-sectional view taken along the XY plane of a multi-channel continuous-shape filter according to an example of the present disclosure. As shown in FIG. 9, the disc 122 may be arranged with three continuous-shape filters. Wherein, the filter 41 may be a continuous-shape filter which is used to scan patient's head, the filter 42 may be a continuous-shape filter which is used to scan patient's shoulder, and the filter 43 may be a continuous-shape filter which is used to scan patient's chest. Each of the body thicknesses of the continuous-shape filters may depend upon the tissue thickness distribution of the examination regions.

In one example, before the CT scanning, the examination region of a patient may be determined by the filter controller 22. If the examination region is the chest of the patient, then the filter drive motor 16 can be used to drive the filter set 12 such that the chest filter 43 may be moved to the position shown in FIG. 9. Thus, the X-ray center beam generated by the X-ray generator 11 may penetrate through the groove bottom of the chest filter 43 and may reach the examination region. After the CT scanning, the filter set 12 may be rotated together with the X-ray generator 11 around the Z-axis. The filter drive motor 16 may drive the disc 122 to rotate around the shaft axis of the drive shaft 121. In the rotation process of the disc 122, the X-ray may substantially penetrate through the groove of the chest filter 43.

Similarly, the examining table 14 may be moved along the Z-axis such that the examination region is switched to patient's shoulder. Under the control of the filter controller 22, the filter drive motor 16 may drive the filter set 12 to move along the X-Y plane. Thus, the X-ray center beam generated by the X-ray generator 11 may penetrate through the center position of the groove bottom of the shoulder filter 42 to perform the CT scanning for the patient's shoulder.

The multi-channel continuous-shape filter of the present disclosure, can meet the requirement of the respective X-ray attenuations for different examination regions. Moreover, the multi-channel continuous-shape filter may also meet the requirement of the X-ray attenuation for the same examination region under different projection angles, which may optimize the intensity distribution of the X-ray more uniform to increase the quality of CT images and reduce the radiation dose for the patient's body.

Figure 10:
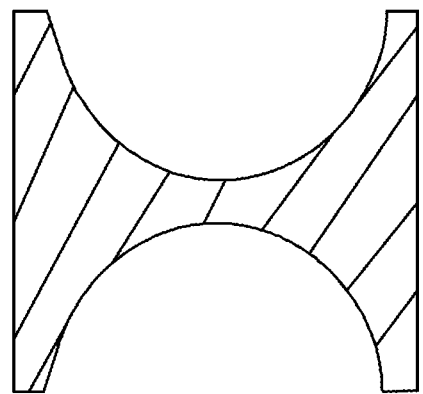
FIG. 10 schematically shows another shape of the radial cross-sectional view according to an example of the present disclosure.

From the aforementioned examples, the shape of the radial cross-sectional view of the filter is a bow tie as an example. FIG. 10 schematically shows another shape of the radial cross-sectional view of the filter according to an example of the present disclosure. The radial cross-section of the filter may be a bi-groove structure shown in FIG. 10. It may achieve the aforementioned effects by using the annular filter with the radial cross-section of the filter being the bi-groove structure.

Figure 11:
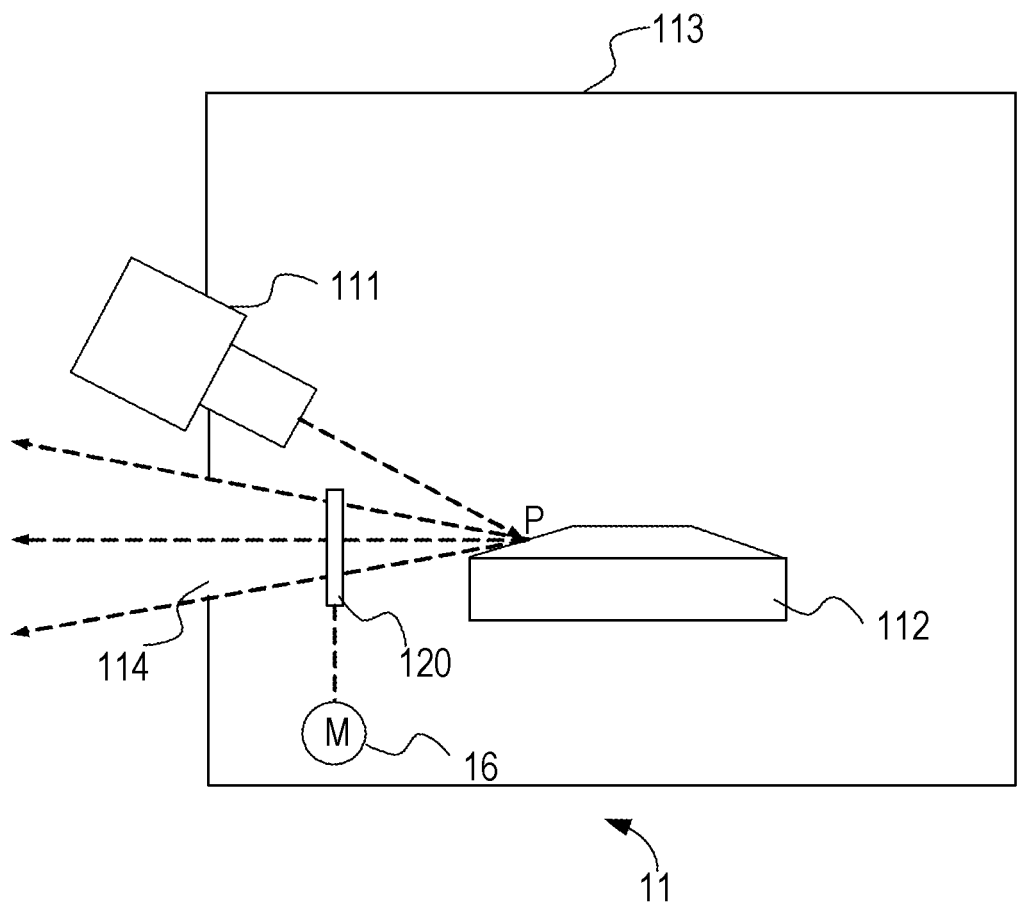
FIG. 11 is a schematic structure diagram of an X-ray generator according to an example of the present disclosure.

In the aforementioned examples, the filter set 12 may be disposed outside the X-ray generator 11 for illustration purposes. In the other example of the present disclose, the filter set 12 may be disposed inside the interior of the X-ray generator 11. FIG. 11 is a schematic structure diagram of an X-ray generator according to an example of the present disclosure. As shown in FIG. 11, the X-ray generator 11 may comprise a cathode electron gun 111, an anode target disc 112, and a housing 113. In the housing 113, there is a window 114 in which the X-ray may be radiated through the window 114. The electron beam emitted by the cathode electron gun 111 may be focused on a focal point P on the anode target disc 112. After electron beam being applied to the anode target disc 112, then it may generate the X-ray which may be radiated through the window 114.

In one example of the present disclosure, the filter set 120 may be disposed inside the cavity of the X-ray generator 11. As shown in FIG. 11, the filter set 120 may be disposed between the window 114 and the focal point P on the anode target disc 112. The filter set 120 may comprise the separable-shape filter, the continuous-shape filter, or the multi-channel continuous-shape filter.

The focal point P may be regarded as a point light source of the X-ray. For scanning an examination region of a subject with the same width, the size of the filter set 12, 120 may be increased as the distance between the filter set 12, 120 to the focal point P is increasing. Thus, in comparison with the arrangement of the filter set 12 being disposed outside the X-ray generator 11, the arrangement of the filter set 120 being disposed inside the X-ray generator 11 may be reduced the space occupied by the filter set. Thus, it may effectively alleviate the space constraints of the filter set.

In addition, the filter may be made of plastic material such as Teflon. The filter may also be made of aluminium alloy. Since the X-ray attenuation of the aluminium alloy may be larger than that of the plastic material under the same thickness, the filter set with the material of the aluminium alloy may reduce the space occupied by the filter set in the interior of the gantry.

Figure 12:
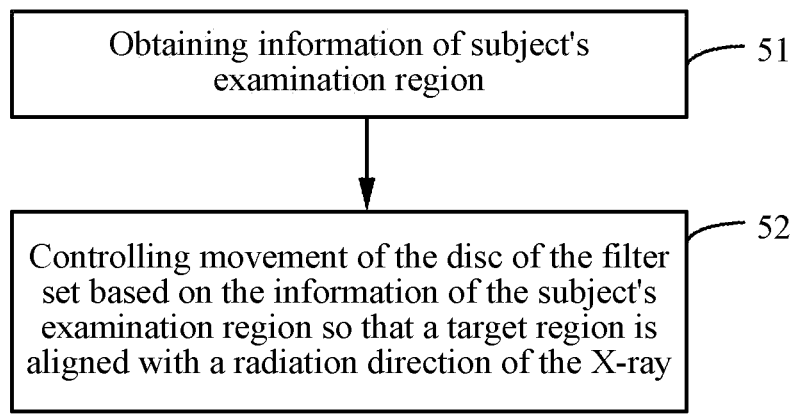
FIG. 12 is a flowchart of a control method of controlling a filter set according to an example of the present disclosure.

Corresponding to the filter set, the present disclosure may provide a control method for controlling the filter set. The control method may be executed by the filter controller 22 shown in FIG. 2. FIG. 12 is a flowchart of a control method of controlling a filter set according to an example of the present disclosure.

In block 51, information of a subject's examination region can be obtained. The subject may be a patient, and the information of subject's examination region may comprise the position of the examination region corresponding to the X-ray generator 11, the tissue thickness distribution of the examination region in the X-Y plane, the requirement of X-ray attenuation, and so on. The information of the subject's examination region can be obtained from a user input. For example, an operator may input the subject's examination region by computer 150.

In block 52, the movement of the disc 122 of the filter set 12 can be controlled based on the information of the subject's examination region so that a target region is aligned with a radiation direction of the X-ray generated by the X-ray generator 11, wherein a body thickness of the target region may meet with the requirement of X-ray attenuation for the subject's examination region.

For example, the target filter of the filter set 12 can be determined according to the tissue thickness distribution of the examination region in the X-Y plane, and the rotation of the disc 122 of the filter set 12 can be controlled such that the target filter is aligned with the radiation direction of the X-ray. Therefore, the X-ray center beam may penetrate through the center position of the target filter and may reach the examination region. Wherein, the X-ray attenuation curves corresponding to the target filter may be coincided with the requirements of X-ray attenuation which may be determined according to the tissue thickness distribution of the examination region.

Figure 13:
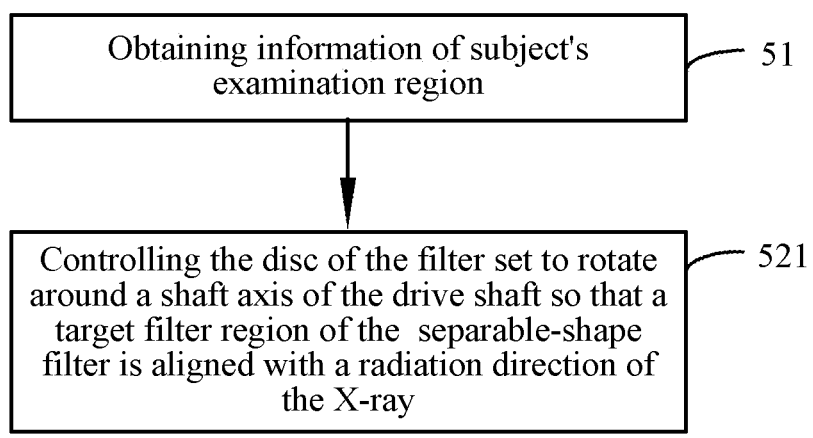
FIG. 13 is a flowchart of a control method of controlling a filter set according to another example of the present disclosure.

FIG. 13 is a flowchart of a control method of controlling a filter set according to another example of the present disclosure. Based on the basis of FIG. 12, the block 52 in FIG. 12 may be implemented as the block 521 in FIG. 13. In block 521, as the disc 122 of the filter set 12 being arranged with a separable-shape filter, it may control the disc 122 to rotate around a shaft axis of the drive shaft 121 so that a region of the target filter is aligned with a radiation direction of the X-ray. The X-ray attenuation curves corresponding to the region of the target filter may be coincided with the requirements of X-ray attenuation, wherein the requirements of X-ray attenuation may be determined according to the tissue thickness distribution of the examination region.

Figure 14:
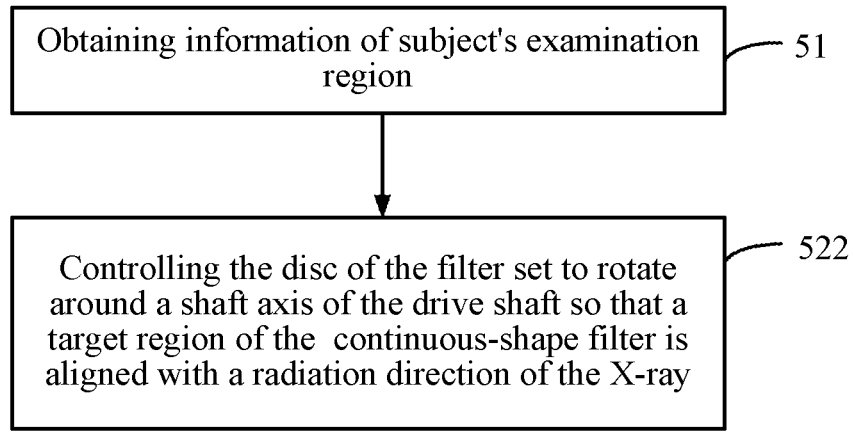
FIG. 14 is a flowchart of a control method of controlling a filter set according to still another example of the present disclosure.

FIG. 14 is a flowchart of a control method of controlling a filter set according to still another example of the present disclosure. Based on the basis of FIG. 12, the block 52 in FIG. 12 may be implemented as the block 522 in FIG. 14. In block 522, the disc 122 of the filter set 12 may be arranged with a continuous-shape filter. According to the requirement of the X-ray attenuation for the examination region under different projection angles, it may control the disc 122 to continuously rotate around a shaft axis of the drive shaft 121 based on a predetermined mode. Thus, in the process of the disc 122 being rotating around the shaft axis of the drive shaft 121, the X-ray may substantially penetrate through the groove of the filter which may meet the requirement of X-ray attenuation for the examination region under the current projection angle.

Figure 15:
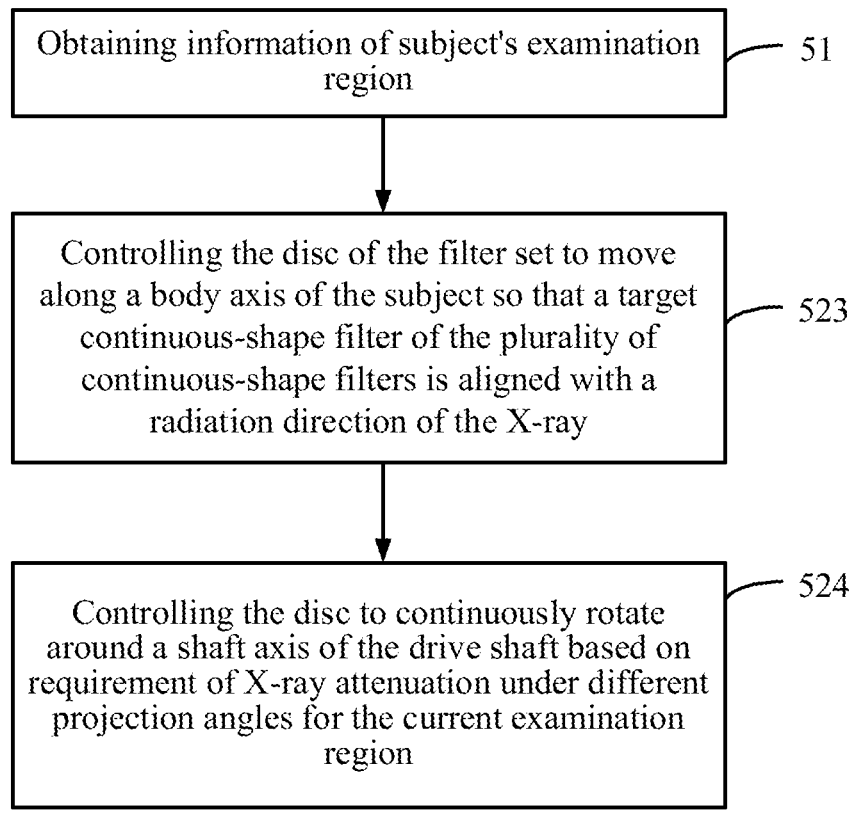
FIG. 15 is a flowchart of a control method of controlling a filter set according to yet another example of the present disclosure.

FIG. 15 is a flowchart of a control method of controlling a filter set according to yet another example of the present disclosure. Based on the basis of FIG. 12, the block 52 in FIG. 12 may be implemented as the block 523 and the block 524 in FIG. 15.

In block 523, as the disc 122 of the filter set 12 being arranged with a plurality of continuous-shape filter, it may control the disc to move along the Z-axis, e.g., a body axis of the subject, so that a target continuous-shape filter of the plurality of continuous-shape filters is aligned with a radiation direction of the X-ray, wherein the target continuous-shape filter is corresponding to the examination region. Therefore, the X-ray center beam may penetrate through the center position of the groove bottom of the target continuous-shape filter.

In block 524, according to the requirement of X-ray attenuation under different projection angles for the current examination region, it may control the disc to continuously rotate around a shaft axis of the drive shaft 121 based on a predetermined mode. Thus, in the process of the disc 122 being rotating around the shaft axis of the drive shaft 121 based on the predetermined mode, the X-ray may substantially penetrate through the groove of the target continuous-shape filter which may meet the requirement of X-ray attenuation for the current examination region under the current projection angle.

Figure 16:
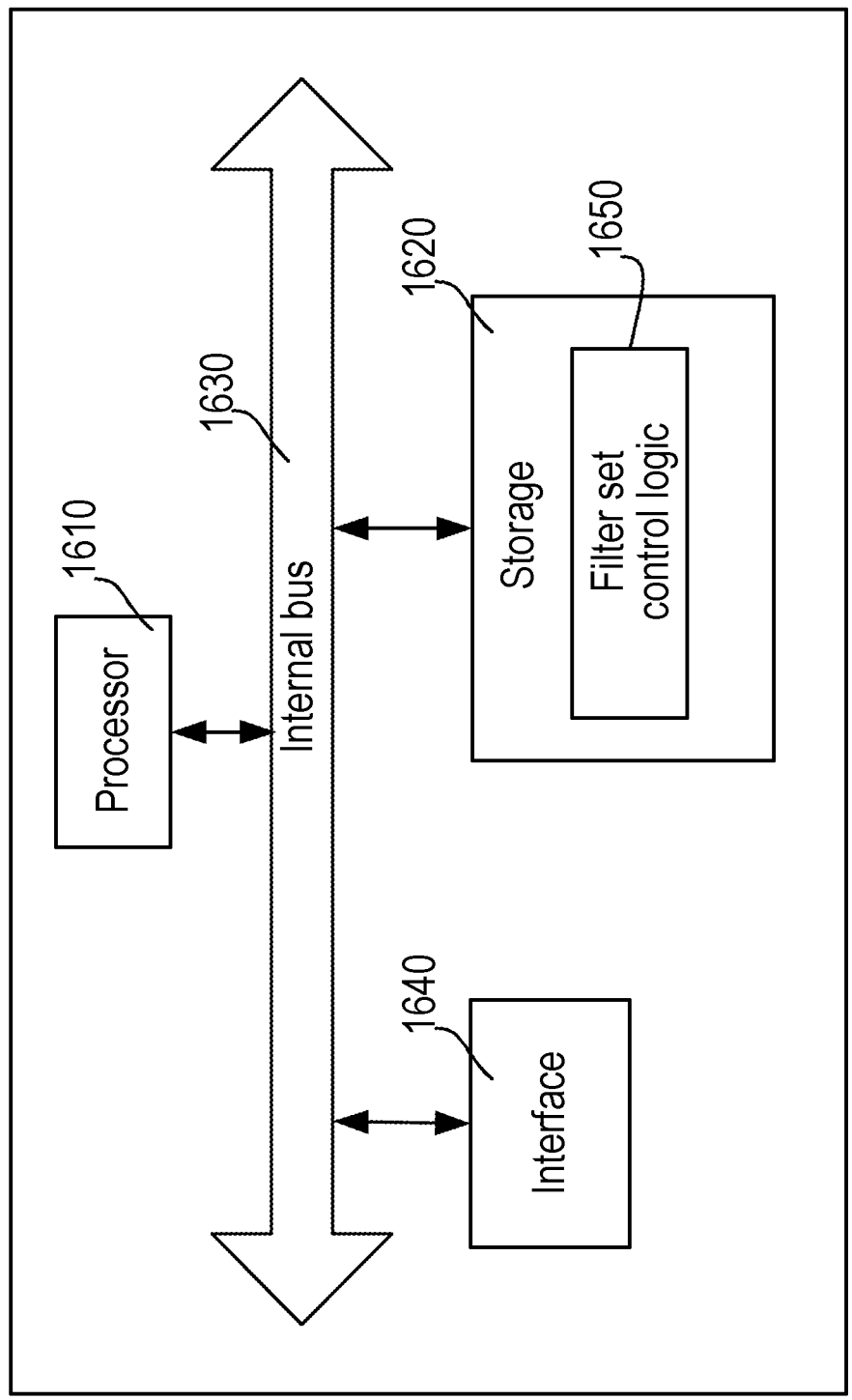
FIG. 16 is a schematic diagram of hardware architecture of an apparatus for controlling a filter set according to an example of the present disclosure.

FIG. 16 is a schematic diagram of hardware architecture of an apparatus for controlling a filter set according to an example of the present disclosure. The apparatus for controlling a filter set may comprise a processor 1610 and a storage 1620. The processor 1610 may be connected to the storage 1620 by an internal bus 1630. In another example, the apparatus for controlling a filter set may further comprise an external interface 1640 which can be communicated with other devices or components.

In another example, as shown in FIG. 16, the storage 1620 and the interface 1640 are accessible by the processor 1610 through the internal bus 1630. The storage 1620 stores the filter set control logic 1650 of machine readable instructions executable by the processor 1610. The storage 1620 in which the machine readable instructions are stored may be a non-volatile memory or storage media including by way of example semiconductor memory devices, e.g., EPROM, EEPROM, DRAM and flash memory devices; magnetic disks, e.g., internal hard disks or removable disks; magneto optical disks; and CD ROM and DVD-ROM disks. The processor 1610 of the apparatus for controlling a filter set may read the instructions of the corresponding modules of the filter set control logic 1650 stored in the storage 1620 and executes the instructions.

Figure 17:
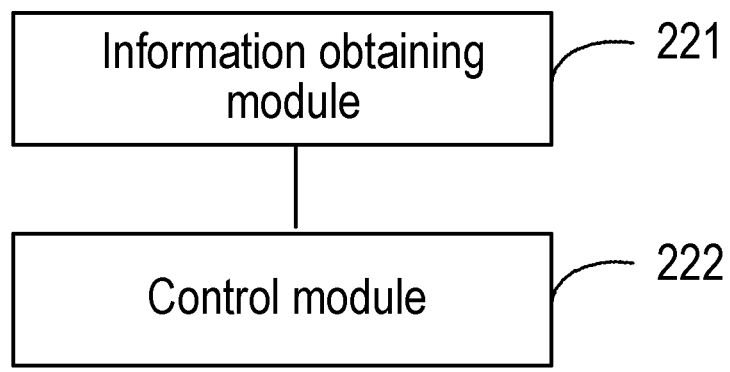
FIG. 17 is a schematic diagram of function modules of filter set control logic according to an example of the present disclosure.

FIG. 17 is a schematic diagram of function modules of the filter set control logic 1650 according to an example of the present disclosure. According to the functions of the filter set control logic 1650, the filter set control logic 1650 may be divided into an information obtaining module 221 and a control module 222.

The information obtaining module 221 may be used to obtain information of patient's examination region, wherein the information of patient's examination region may comprise the cross-section shape of the examination region along the body axis and the tissue thickness distributions of the examination region under different projection angles, and so on.

The control module 222 may control the movement of the disc 122 of the filter set 12 based on the information of patient's examination region so that a target region of the filter set 12 is aligned with a radiation direction of the X-ray, wherein the target region may meet the requirement of X-ray attenuation of the examination region. For example, it may determine a target filter of the filter set 12 according to the tissue thickness distribution of the examination region in the X-Y plane, and may control the rotation of the disc 122 in the filter set 12 such that the target filter is aligned with the radiation direction of the X-ray. Therefore, the X-ray center beam may penetrate through the center position of the target filter and may reach the examination region. Wherein, the X-ray attenuation curves corresponding to the target filter may be coincided with the requirements of X-ray attenuation which may be determined according to the tissue thickness distribution of the examination region.

In one example of the present disclosure, the disc 122 of the filter set 12 may be arranged with a separable-shape filter. The control module 222 may control the disc 122 to rotate around a shaft axis of the drive shaft 121 so that a region of the target filter is aligned with a radiation direction of the X-ray. The X-ray center beam may penetrate through the center position of the target filter region and may reach the examination region. The X-ray attenuation curves corresponding to the region of the target filter may be coincided with the requirements of X-ray attenuation, wherein the requirements of X-ray attenuation may be determined according to the tissue thickness distribution of the examination region.

In another example of the present disclosure, the disc 122 of the filter set 12 may be arranged with a continuous-shape filter. According to the requirement of the X-ray attenuation for the examination region under different projection angles, the control module 222 may control the disc 122 to continuously rotate around a shaft axis of the drive shaft 121 based on a predetermined mode. Thus, the X-ray may substantially penetrate through the region of the filter which may meet the requirement of X-ray attenuation for the examination region under the current projection angle. The predetermined mode may comprise the starting position based on an initial viewing angle, the rotation speed based on the patient's examination region, and so on.

In another example of the present disclosure, the disc 122 of the filter set 12 may be arranged with the multi-channel continuous-shape filter. The control module 222 may control the disc 122 to move along the Z-axis so that a target continuous-shape filter is aligned with a radiation direction of the X-ray, wherein the target continuous-shape filter is corresponding to the examination region. Therefore, the X-ray center beam may penetrate through the center position of the groove bottom of the target continuous-shape filter. According to the requirement of X-ray attenuation under different projection angles for the current examination region, the control module 222 may control the disc 122 to continuously rotate around the shaft axis of the drive shaft 121 based on a predetermined mode. Thus, in the process of the disc 122 being rotating around the shaft axis of the drive shaft 121, the X-ray may substantially penetrate through the groove of the target continuous-shape filter which may meet the requirement of X-ray attenuation for the current examination region under the current projection angle.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be disposed in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the above description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on. The terms "be used to" and "be configured to" can be used interchangeably.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. Accordingly, other embodiments are within the scope of the following claims.

The invention claimed is:

1. A filter set of a computed tomography (CT) scanning device, comprising:
   a disc;
   a filter disposed on the disc, the filter having a substantially annular groove structure, a body thickness of the annular groove structure varying in a circumferential direction and a radial direction, wherein the filter comprises a plurality of annular grooves separable in the radial direction, wherein the plurality of annular grooves are parallel with each other in the radial direction, and wherein a body thickness of each of the plurality of annular grooves continuously varies in the circumferential direction of the disc; and
   a drive shaft connected to the disc, a shaft axis of the drive shaft being parallel to a radiation direction of X-ray of the CT scanning device, the disc being configured to rotate around the shaft axis of the drive shaft,
   wherein the annular groove structure extends along the shaft axis, and an outer diameter of a radial cross-sectional shape of the annular groove structure gradually varies along the shaft axis.

2. The filter set according to claim 1, wherein a radial cross-sectional shape of each of the plurality of annular grooves of the filter is a bow tie.

3. The filter set according to claim 1, wherein the drive shaft penetrates through an opening defined by the annular groove structure along the shaft axis.

4. A computed tomography (CT) scanning device comprising:
   a gantry;
   an X-ray generator disposed in an interior of the gantry and configured to rotate together with the gantry around a body axis of a subject;
   a filter set disposed in the interior of the gantry, the filter set being configured to be located between the X-ray generator and the subject and to rotate together with the gantry around the body axis of the subject, the filter set comprising:
      a disc;
      a filter disposed on the disc, the filter having a substantially annular groove structure, a body thickness of the annular groove structure varying in a circumferential direction and a radial direction, wherein the filter comprises a plurality of annular grooves separable in the radial direction, wherein the plurality of annular grooves are parallel with each other in the radial direction, and wherein a body thickness of each of the plurality of annular grooves continuously varies in the circumferential direction of the disc; and a drive shaft connected to the disc, a shaft axis of the drive shaft being parallel to a radiation direction of X-ray generated by the X-ray generator, the disc being configured to rotate around the shaft axis, wherein the annular groove structure extends along the shaft axis, and an outer diameter of a radial cross-sectional shape of the annular groove structure gradually varies along the shaft axis;

a detector disposed in the interior of the gantry and located at an opposite side of the X-ray generator, the detector being configured to rotate together with the gantry around the body axis of the subject and to receive the X-ray generated by the X-ray generator and filtered by the filter set; and a drive motor connected to the drive shaft and configured to drive the drive shaft such that the disc rotates around the shaft axis of the drive shaft.

5. The CT scanning device according to claim 4, wherein the gantry is a substantially annular structure, and wherein the filter set is located inside the gantry and opposite to the X-ray generator in a radial direction of the substantially annular structure.

6. The CT scanning device according to claim 4, wherein the filter is located between an anode focus and a radiation window in an interior cavity of the X-ray generator.

7. The CT scanning device according to claim 4, wherein the drive shaft penetrates through an opening defined by the annular groove structure along the shaft axis.

8. A method of controlling a filter set of a computed tomography (CT) scanning device, the method comprising:

obtaining information of an examination region of a subject; and controlling movement of a disc of the filter set based on the determined information of the examination region, such that a target region of a filter of the filter set disposed on the disc is aligned with a radiation direction of an X-ray of the CT scanning device, wherein a body thickness of the target region of the filter corresponds to a respective X-ray attenuation for the examination region, wherein the filter has a substantially annular groove structure, a body thickness of the annular groove structure varying in a circumferential direction and a radial direction, wherein the filter comprises a plurality of annular grooves separable in the radial direction, wherein the plurality of annular grooves are parallel with each other in the radial direction, and wherein a body thickness of each of the plurality of annular grooves continuously varies in the circumferential direction of the disc, wherein the disc is connected to a drive shaft of the filter set that has a shaft axis parallel to the radiation direction of the X-ray, the disc being configured to rotate around the shaft axis, and wherein the annular groove structure extends along the shaft axis, and an outer diameter of a radial cross-sectional shape of the annular groove structure gradually varies along the shaft axis.

9. The method according to claim 8, wherein controlling the movement of the disc of the filter set comprises:

controlling the disc to move along a body axis of the subject such that a target annular groove of the plurality of annular grooves is aligned with the radiation direction of the X-ray, wherein the body thickness of the target annular groove corresponds to the respective X-ray attenuation for the examination region; and controlling the disc to continuously rotate around the shaft axis of the drive shaft based on respective X-ray attenuations under different projection angles for the examination region.

10. The method according to claim 8, wherein the drive shaft penetrates through an opening defined by the annular groove structure along the shaft axis.

* * * * *

UNITED STATES PATENT AND TRADEMARK OFFICE
CERTIFICATE OF CORRECTION

PATENT NO.        : 10,709,396 B2
APPLICATION NO.   : 15/373811
DATED             : July 14, 2020
INVENTOR(S)       : Shanshan Lou and Hongbo Wang Page 1 of 1

It is certified that error appears in the above-identified patent and that said Letters Patent is hereby corrected as shown below:

On the Title Page

Item [73] replace "Shanghai (CN)" with --Beijing (CN)--.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*